(12) United States Patent
Marka et al.

(10) Patent No.: US 8,292,804 B2
(45) Date of Patent: Oct. 23, 2012

(54) SURGICAL LAMP BEAM ARRANGEMENT

(75) Inventors: Rudolf Marka, Ismaning (DE); Rouven Rosenheimer, Munich (DE); Dirk Fritze, Emmering (DE)

(73) Assignee: Trumpf Medizin Systeme GmbH + Co. KG, Saalfeld (DE)

( * ) Notice: Subject to any disclaimer, the term of this patent is extended or adjusted under 35 U.S.C. 154(b) by 142 days.

(21) Appl. No.: 12/487,239

(22) Filed: Jun. 18, 2009

(65) Prior Publication Data

US 2009/0318772 A1     Dec. 24, 2009

(30) Foreign Application Priority Data

Jun. 20, 2008    (EP) ..................................... 08011296

(51) Int. Cl.
*A61B 1/06*    (2006.01)
(52) U.S. Cl. ....................................................... 600/249
(58) Field of Classification Search .................. 362/285, 362/382, 147, 427; 600/249
See application file for complete search history.

(56) References Cited

U.S. PATENT DOCUMENTS

| | | | | |
|---|---|---|---|---|
| 3,437,803 | A * | 4/1969 | Schafer et al. ..................... | 362/8 |
| 3,786,243 | A | 1/1974 | Ilzig et al. | |
| 4,064,425 | A * | 12/1977 | Masson .......................... | 362/33 |
| 4,884,008 | A | 11/1989 | Bossler et al. | |
| 5,038,261 | A | 8/1991 | Kloos | |
| 5,068,767 | A * | 11/1991 | Koyama .......................... | 362/33 |
| 5,257,173 | A * | 10/1993 | Ohmamyuda et al. ......... | 362/235 |
| 5,383,105 | A | 1/1995 | Agut | |
| 7,311,410 | B2 * | 12/2007 | Marka ............................. | 362/33 |
| 7,401,944 | B2 * | 7/2008 | Hunerbein et al. ............. | 362/241 |
| 7,600,894 | B1 * | 10/2009 | Simon ............................ | 362/244 |
| 7,706,683 | B2 * | 4/2010 | Rossner et al. ................. | 396/429 |
| 7,911,351 | B2 * | 3/2011 | Mackenzie et al. ............ | 340/638 |
| 2005/0083594 | A1 | 4/2005 | Marchese et al. | |
| 2005/0195599 | A1 | 9/2005 | Marka | |
| 2005/0195601 | A1 | 9/2005 | Marka | |
| 2008/0232086 | A1 * | 9/2008 | Marka et al. .................... | 362/85 |

FOREIGN PATENT DOCUMENTS

| | | |
|---|---|---|
| DE | 1197827 | 8/1965 |
| DE | 1597915 | 10/1970 |
| DE | 2141351 | 3/1973 |
| DE | 19839827 | 3/2000 |
| DE | 19839827 A1 | 3/2000 |
| DE | 20104820 U1 | 9/2001 |
| DE | 20316756 | 3/2005 |
| EP | 0299196 | 1/1989 |
| EP | 0422331 | 4/1991 |
| EP | 1526327 | 4/2005 |
| EP | 1568934 | 8/2005 |
| EP | 1938768 | 7/2008 |
| EP | 1568935 | 8/2008 |

(Continued)

OTHER PUBLICATIONS

European Search Report for corresponding European Patent Application No. EP 08014768, mailed Dec. 2, 2008, 5 pages.

(Continued)

*Primary Examiner* — Alvin Stewart
*Assistant Examiner* — James Palmer
(74) *Attorney, Agent, or Firm* — Fish & Richardson P.C.

(57) ABSTRACT

A surgical lamp includes a lamp body with illuminants. Axes of bundled light beams emitted by the illuminants intersect a central axis at different positions along the central axis.

20 Claims, 3 Drawing Sheets

FOREIGN PATENT DOCUMENTS

| | | |
|---|---|---|
| GB | 1122968 | 8/1968 |
| JP | 2004288474 A | 10/2004 |
| JP | 2006156074 A | 6/2006 |
| WO | 2007036581 A1 | 4/2007 |
| WO | 2007086770 | 8/2007 |
| WO | WO/2007/086770 * | 8/2007 |

OTHER PUBLICATIONS

European Search Report for corresponding European Patent Application No. EP 08011296, mailed Dec. 9, 2008, 7 pages.

English translation of Opposition of Berchtold Holding GmbH for corresponding European Application No. 2 136 128 B1, issued by the European Patent Office on Oct. 31, 2011, 19 pages, with cited documents K1: Catalogue "Chomophare" of Gerr. Martin (May 1989); K1-Z: Figure on p. 9 of K1 with delineated axes; D1-Z: Fig. 6A of WO 2007/036581 with delineated axis; D2-Z: Fig. 3 of DE 201 04 820 with delineated axes; D2-Z2: Fig. 2 of DE 201 04 820 with delineated axes; D3-Z: Fig. 6 of EP 1 568 934 with delineated axes.

English translation of Opposition of Dr. Mach GmbH for corresponding European Application No. 2 136 128 B1, issued by the European Patent Office on Oct. 31, 2011, 25 pages, with cited documents Leaflet "Hanaulux 2000"—Heraeus Med GmbH; Leaflet "Prismalix"—Maquet GmbH & Co. KG and Maquet SA; Leaflet "Prismatic"—Alm S.A.; OV Mach—obvious prior use of "Mach AF700/5001400 with Dr. Mach INTCON".

\* cited by examiner

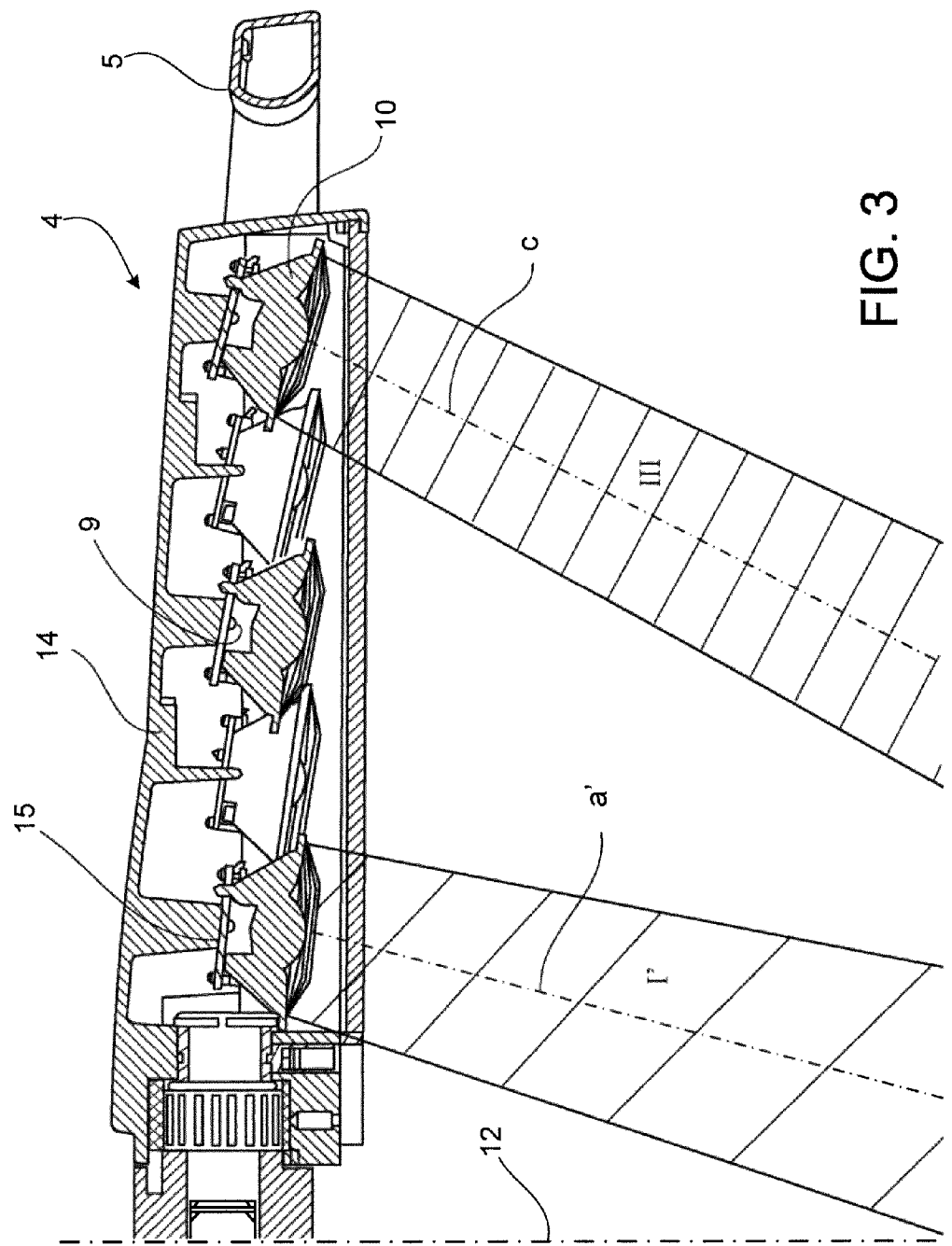

SURGICAL LAMP BEAM ARRANGEMENT

CROSS REFERENCE TO RELATED APPLICATION

This application claims priority under 35 U.S.C. §119(a) to European Patent Application No. 08 011 296.4, filed Jun. 20, 2008, the entire contents of which are hereby incorporated by reference.

TECHNICAL FIELD

The invention relates to a surgical lamp beam arrangement.

BACKGROUND

One possibility for the design of surgical lamps are so-called single reflector lamps. In such lamps, the light source is a halogen lamp or a gas discharge lamp, which is arranged in the focal point of a large reflector having a diameter of about 500 mm to 1000 mm. By displacing the light source along the central axis of the reflector more or less out of the optimum focal point or into the optimum focal point, the diameter of the light field, i.e., the illuminated diameter in the operating field is enlarged or narrowed and the focal point is shifted, i.e., the distance between the location which is illuminated as the brightest where the reflected light beams intersect and the lamp body of the surgical lamp is modified along a central axis of the lamp body. Thereby, a complex mechanism which allows a reliable and smooth-running operation without any big effort of operation for the operator is necessary.

Multi-reflector lamps constitute another construction. Multi-reflector lamps typically include a central spotlight or a central light module, which is rigidly fixed to the lamp body, and several spotlights or light modules, which are annularly arranged about the central spotlight or the central light module. A change of direction of the light emitted by the outer spotlights or light modules is achieved by radially pivotable illuminants or reflectors, or the spotlights or light modules themselves are radially pivotably adjustable so that the distance between the focal point of the light beams of the outer spotlights or light modules changes and the lamp body along the central axis changes. A complex mechanism for synchronously reliably adjusting of the outer illuminants, reflectors or light modules is necessary for such multi-reflector lamps.

Other kinds of surgical lamps are designed without any adjustability of the light field diameter or of the position of the focal point along the central axis. In such lamps, the light characteristics, diameter of the light field and focal point are optimally adjusted for one operating point. A modification of the light field diameter is generally only possible by varying the distance between the lamp body and the operation field. Varying the distance of the focal point is not generally possible. When using multi-reflector lamps, there is a risk that the light field seems no longer homogenous but several light points are projected in the operation area when the distance between the lamp body and the operation site is small.

SUMMARY

In one aspect of the invention, a surgical lamp includes a lamp body having a central axis. The lamp body includes at least first and second illuminants. The first illuminant is configured to emit a first bundle of light beams, and the second illuminant is configured to emit a second bundle of light beams. An axis of the first bundle of light beams is directed to a first point on the central axis, an axis of the second bundle of light beams is directed to a second point on the central axis, and the first and second points are spaced apart from one another along the central axis such that the first and second points are positioned at different distances from the lamp body along the central axis.

In some embodiments, the surgical lamp further includes a device adapted to dim the illuminants and to turn the illuminants on and off.

In some embodiments, the device is a current regulator.

In some embodiments, the illuminants are arranged in a plane that is perpendicular to the central axis.

In some embodiments, the surgical lamp comprises at least first and second groups of illuminants, the first and second groups of illuminants are configured to generate light fields, the illuminants of the first group are arranged so that axes of light beams emitted by the illuminants of the first group are directed to the first point on the central axis, and the illuminants of the second group are arranged so that axes of light beams emitted by the illuminants of the second group are directed to the second point on the central axis.

In some embodiments, the first group of illuminants includes the first illuminant, and the second group of illuminants includes the second illuminant.

In some embodiments, the illuminants of at least one of the groups are evenly distributed across the lamp body.

In some embodiments, the illuminants of at least one of the groups are arranged in an annular pattern about the central axis of the lamp body.

In some embodiments, each of the illuminants is attached to an inclined fixing face of a housing of the lamp body.

In some embodiments, each of the inclined faces has an axis that extends perpendicularly relative to the inclined face, and the axes of the inclined faces to which the illuminants of one of the groups are attached intersect the central axis at a common location along the central axis.

In some embodiments, the surgical lamp further includes a control device adapted to operate the groups of illuminants in a manner so that the group of illuminants emitting light beams having axes nearest a desired operation site have the greatest brightness.

In some embodiments, the illuminants are attached to inclined fixing faces of a housing of the lamp body.

In some embodiments, the illuminants include light emitting diodes.

In some embodiments, the illuminants include light emitting diodes and refractors.

In some embodiments, the illuminants include light emitting diodes and reflectors.

In some embodiments, the surgical lamp further includes a control device adapted to operate the illuminants in a manner so that the one of the first and second illuminants that emits the bundle of light beams whose axis intersects the central axis of the lamp body nearest an operation site has the greatest brightness.

In some embodiments, the surgical lamp comprises a distance sensor configured to measure a distance between the lamp body and the operation site.

In some embodiments, the distance sensor is adapted to transmit distance information to the control device, and the control device is adapted to operate the illuminants based on the distance information received from the distance sensor.

In some embodiments, the control device is adapted to operate the one of the first and second illuminants configured to emit a bundle of light beams whose axis is nearest the operation site at a greater brightness than the other of the first and second illuminants.

In some embodiments, the surgical lamp includes a brightness sensor configured to measure brightness at the operation site.

In some embodiments, the brightness sensor is adapted to transmit brightness information to the control device.

In some embodiments, the surgical lamp includes an actuator that is adapted to transmit actuation information to the control device.

Embodiments can include one or more of the following advantages.

In some embodiments, the surgical lamp economically provides the opportunity to modify the diameter of the light field and the distance between the focal point and the lamp body.

In certain embodiments, the surgical lamp provides the opportunity to modify the diameter of the light field and the distance between the focal point and the lamp body by a specific arrangement and control of the illuminants. This can be done without any mechanical adjusting devices.

Other aspects, features, and advantages of the invention are in the description, drawings, and claims.

DESCRIPTION OF DRAWINGS

FIG. 3 is a sectional view of the lamp body with multiple illuminants.

DETAILED DESCRIPTION

Figure 1:
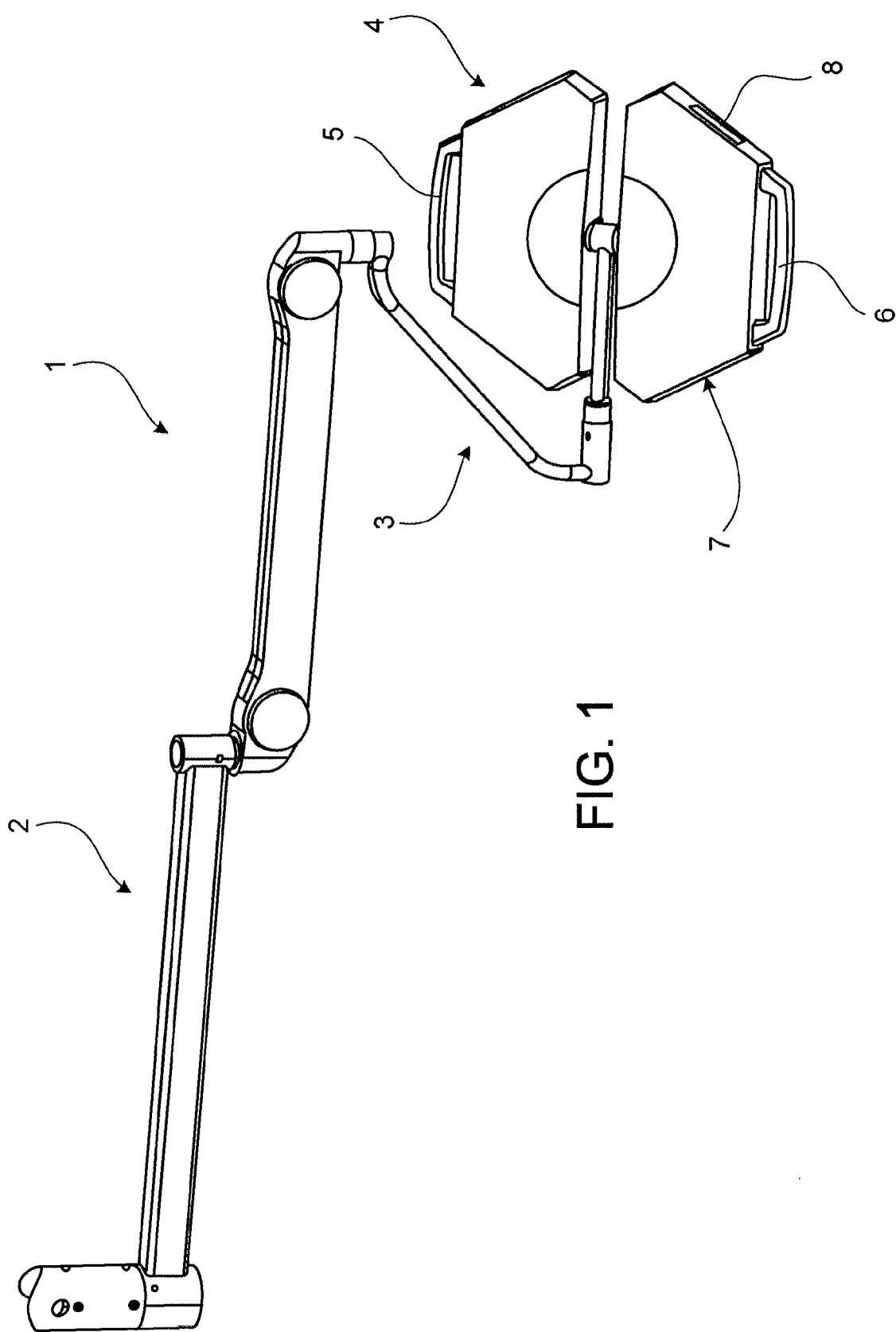
FIG. 1 is a perspective view of a surgical lamp.

FIG. 1 is a perspective view of a surgical lamp 1 that includes a carrying system 2, a suspension system 3, and a lamp body 4. The carrying system is fixed to a ceiling of a room, a wall, or a movable stand. Due to the carrying system 2 and the suspension system 3, the lamp body 4 is positionable at any of various different arbitrary positions and orientations within the range of action. A light emitting area is arranged on nearly the entire area of the opposite side of the lamp body 4, which is directed to an operation field at a certain distance from the lamp body 4 when used.

For non-sterile positioning of the lamp body 4, handles 5, 6 are attached to both halves of the lamp body 4. Both halves of the lamp body 4 are attached to another in a torsion-proof manner so that during pivoting of one of the halves, the other half accordingly follows to keep the light emitting areas in one plane.

A control device 7 is arranged inside the lamp body 4. However, the control device 7 need not necessarily be attached inside the lamp body 4. Rather, the control device 7 can be housed in a discrete housing that is attached to the lamp body 4 or to the suspension device 3. The control device 7 can alternatively be located in an operation unit, which is located in a medical supply unit or in/at a wall.

An operation device 8 is arranged on the outside of the lamp body 4. Alternatively, the operation device 8 can be arranged in a separate housing that is located at the lamp body 4, at the suspension device 3, in a medical supply unit, or in/at a wall.

Figure 2:
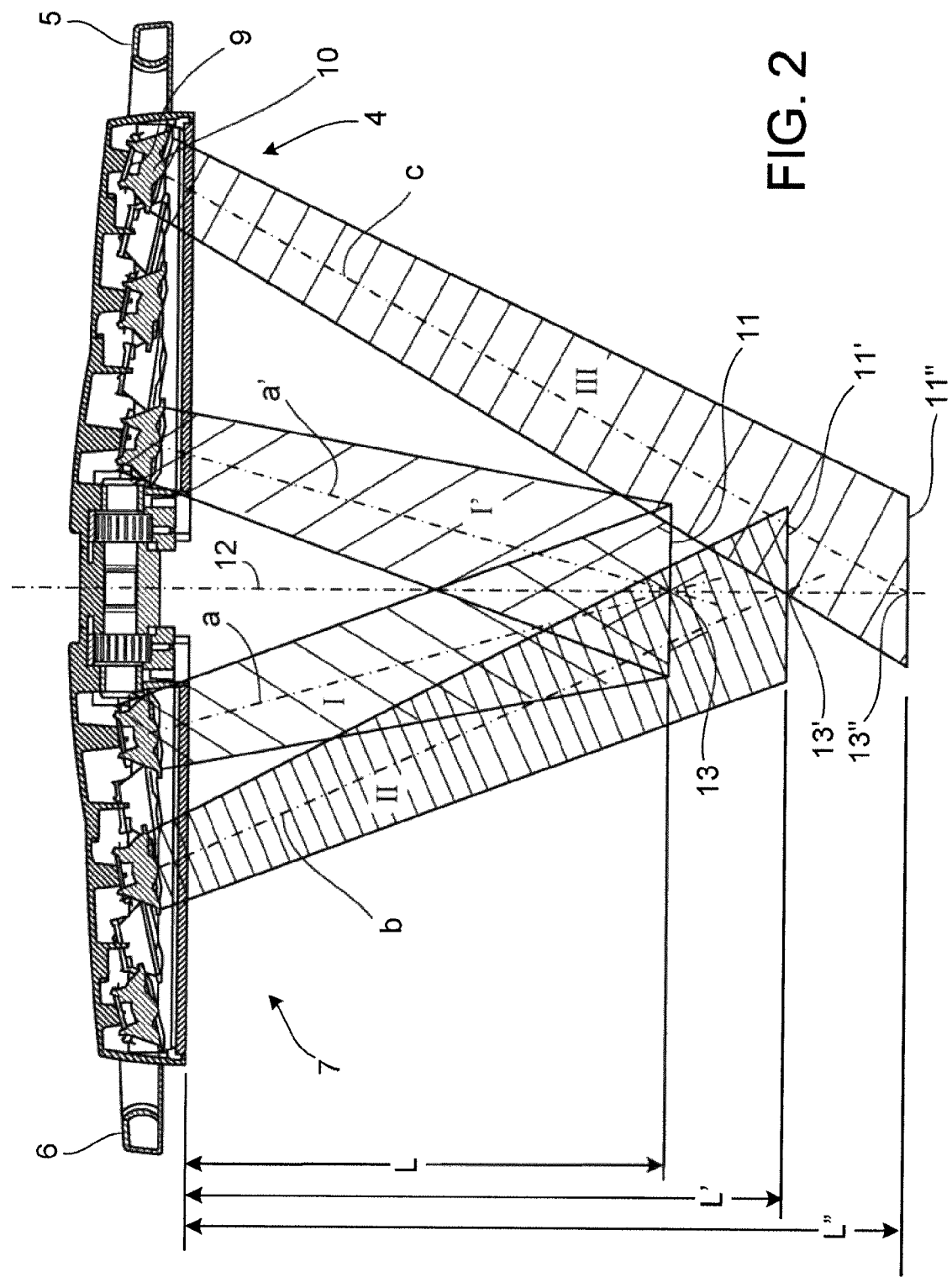
FIG. 2 is a sectional view of a lamp body, showing paths of light beams extending from multiple different illuminants in the lamp body.

FIG. 2 is a sectional view of the lamp body 4 in which multiple illuminants 9 are provided. The lamp body has a central axis 12 that extends perpendicular to a plane in which the illuminants 9 are arranged. The illuminants 9 are attached annularly or according to the shape of the lamp body 4.

Each illuminant 9 is provided with a device for bundling of the light. In some embodiments, as shown in FIG. 2, a refractor 10 is used to bundle the light. Alternatively, a reflector can be used to bundle the light. Instead of using separate refractors or reflectors, illuminants having an integrated device for bundling the light can be used.

The bundled light of the illuminants 9 is emitted in a bundle of light beams I, I', II, III out of the refractor 10. The light beams I, I', II, III have axes a, a', b, c, respectively. The bundle of light beams I and I' illuminate a whole light field 11, and the bundle of light beams II and III illuminate whole light fields 11' and 11", respectively.

The illuminants 9 with the refractors 10 are attached to the lamp body 4 in an inclined manner. As a result, the axes a and a' of the bundles of light beams I and I' intersect the central axis 12 at an intersection point 13. Similarly, the axes b and c of the bundles of light beams II and III intersect the central axis 12 at intersection points 13' and 13", respectively.

The generation of the light field 11 is described below. The generation of the other light fields 11', 11" is performed in an analogous manner, and thus is not separately described.

The bundles of light beams I, I' overlap one another in a plane that is perpendicular to the central axis 12 and is at a distance L from the lamp body 4. Both axes a, a' of the light beams I, I' intersect the central axis 12 at the intersection point 13. The intersection point 13 is a focal point. Thus, the light beams I, I' completely overlap and together generate the light field 11. The light field 11 has a diameter D and a defined distribution of the light intensity across the diameter of the light field, which is normatively prescribed.

In the cross-sectional view of FIG. 2, only two illuminants 9 are shown as generating the light field 11. However, the light field 11 is produced by a sheaf or collection of bundles of light beams I, I' that are emitted by the illuminants 9. The bundles of light beams are evenly distributed across the light emitting area, and the axes of the light beams all intersect at the intersection point 13.

The illuminants 9 are evenly distributed in the plane to shine beneath an object that is positioned between the lamp body 4 and the operation field. For example, if one bundle of light beams is blocked by the object, the light beams emitted by the other illuminants will be unaffected by the object and will thus continue to illuminate the light field. This arrangement helps to avoid or reduce shadowing.

In FIG. 2, the bundles of light beams II, III for producing the light fields 11', 11" are each depicted as being emitted from a single illuminant 9. However, the light fields 11, 11' are produced by sheaves or collections of the bundles of light beams II, III, respectively, which intersect at the intersection points 13' and 13" and constitute focal points at the distances L', L".

Due to the standard distance of 100 cm between the lamp body 4 and the operation site, the following distances were found to be advantageous in empirical tests: L=about 90 cm; L'=about 100 cm; and L"=about 110 cm. Those can be defined as designated distances. The distances L, L', L" correspond to the respective distance between the lamp body 4 and the operation field on which the light field 11, 11', 11" is projected. Subject to the size of the lamp body 4, the values can differ.

When using multiple illuminants 9 that are directed to a light field 11, 11', 11", illuminants 9 having different colors can be used. Thereby, it is possible to adjust the resulting color temperature of the light in a certain range of color temperature.

In some embodiments, the illuminants 9 include light emitting diodes (LEDs). However, they may alternatively include halogen lamps or gas discharge lamps. If necessary, the illuminants 9 can be provided with color filters.

The control device 7 is arranged in the lamp body 4. The control device 7 includes means for dimming and switching on and off of the illuminants 9, such as current regulators, means for transmitting of switching commands and setting commands of the switching elements and setting elements of the operation device 8, a storage area for storing of operation parameters, and a CPU that calculates and determines the necessary adjustments for the means for dimming and switching on and off of the illuminants 9 from the switching and setting commands, based on stored operation parameters.

The control device 7 is connected to the illuminants 9, which are controlled in groups. Each group includes several illuminants 9 that are controlled with the same performance parameters. The light beams I, I', II, III of the illuminants 9 within each group have identical intersection point 13, 13', 13" with the central axis 12. It is possible for the light beams I, I', II, III of the illuminants 9 of several groups to be directed to the same intersection point 13, 13', 13".

The control device 7 is also connected to the operation device 8. The operation device 8 includes an element for switching the surgical lamp 1 on and off, an element for setting the distance between the lamp body 4 and the light fields 11, 11', 11", and an element for setting the brightness of the light fields 11, 11', 11".

The element for switching the surgical lamp 1 on and off switches the surgical lamp 1 from a standby-mode in which the illuminants 9 do not shine to an operating mode. Thereby, the illuminants 9 are controlled according to the setting of the setting elements. For completely switching off the surgical lamp 1 by switching off the current supply, an external main switch is provided.

The element for setting the distance between the light fields 11, 11', 11" and the lamp body 4 transmits information regarding the distance between the light field 11, 11', 11" and the lamp body 4 to the control device 7. The surgical lamp is adjusted in accordance with the transmitted information. In this embodiment, the element for setting the distance can be set to the three distances L, L' and L". In alternative embodiments, an element for setting the distance of further discrete distance values or for a stepless distance setting is possible.

When the surgical lamp 1 is operated at a set distance that corresponds to one of the designated distances L, L', L" to which the light beams I, I', II, III are directed, the illuminants 9 that emit the relevant light beam(s) I, I', II, III are driven with enlarged power. In embodiments in which the set distance is 90 cm, for example, the illuminants 9 that emit the light beams I, I', the axes a, a' of which intersect the central axis 12 at the intersection point 13 at the distance L and generate the light field 11, are driven with enlarged power. Analogously, when the set distance is 100 cm, the illuminants 9 that emit the light beams II, the axes of which intersect the central axis 12 at the intersection point 13', are driven with enlarged power. And, when the set distance is 110 cm, the illuminants 9 that emit the light beams III, the axes c of which intersect the central axis 12 at the intersection point 13", are driven with enlarged power. Driven with enlarged power means that the respective illuminants are driven with maximum power when the surgical lamp is adjusted to maximum brightness. For achieving the determined luminosity, the illuminants 9, the light beams of which are directed to the adjacent intersection points 13, 13', 13", are driven with a defined power. The respective power adjustments are empirically detected and stored in the control device 7. When set to a lower brightness setting, the power values are proportionally changed.

In some embodiments, only the illuminants 9 whose sheaves of bundled light beams I, I', II, III are directed to the distance that corresponds to one of the designated distances are activated. When the set distance does not correspond to one of the designated distances L, L', L", the control device 7 activates those illuminants for which the intersection point 13, 13', 13" of the axes a, a', b, c of their light beams I, I', II, III adjoins to the set distance. For example, the illuminants 9 that emit the light beams II and III are driven when the set distance is between the distances L' and L". The light beams II and III together constitute a resulting light beam having a greater brightness than the separate light beams II and III. The intersection point of the axis of the resulting light beam is between the intersection points 13' and 13" of the axes b and c with the central axis 12. The brightness of the illuminants 9 generating the light beams II and III is coordinated in such a way that the axis of the resulting light beam intersects the central axis at the set distance. The illuminants 9 forming the light beams III are adjusted brighter and the illuminants 9 forming the light beams II are adjusted darker when the set distance is closer to L". When the set distance is closer to L', the illuminants 9 forming the light beams II are adjusted brighter and the illuminants 9 forming the light beams III are adjusted darker.

With these settings, when the set distance corresponds to the actual distance, the light field fulfills the normative requirements regarding the distribution of the brightness in the light field at these settings. With settings in which the set distance does not correspond to the actual distance, the distribution of the brightness in the light field is modified. As a result, the surgical lamp 1 provides the opportunity to adjust the distribution of the brightness in the light field according to the requirements of the surgeon.

When the light beams III are enhanced, i.e., when the distance setting element is set to the distance L", the light field increases if the actual distance is smaller than L" and the brightness in the center of the light field decreases. Also, the light field and the brightness in the center of the light field decrease when the light beams I are enhanced, i.e., when the distance setting element is set to the distance L, if the actual distance is greater than L.

The element for setting brightness transmits setting information about the set general brightness of the surgical lamp 1 to the control device 7. The means for dimming and switching the surgical lamp 1 on and off are driven by the control device 7 in such a way that the distribution of brightness of the several illuminants remains unchanged and only the general brightness is changed.

The performance parameters for the settings are empirically determined and stored in the storage area of the control device 7.

In some embodiments, the surgical lamp 1 includes a distance sensor for measuring the distance between the lamp body 4 and the operation site and means for transmitting the distance to the control device 7. By detecting the distance of the lamp body 4 to the operation site and transmitting the distance information to the control device 7, the control device 7 is capable of adjusting the point having the maximum resulting brightness in the distance of the lamp body 7 to the surgical site so that the operation site is illuminated with the maximum brightness.

In certain embodiments, the surgical lamp 1 includes a brightness sensor that measures the brightness at the operation site and means for transmitting the brightness information to the control device 7. One possibility is to detect the brightness in the center of the light field and another possibility is to detect the average brightness in the entire light field. By detecting the brightness and transmitting the brightness information to the control device 7, the control device 7 is capable of adjusting the point having the maximum resulting brightness in the distance of the lamp body 4 so that the identical detection area of the operation site is illuminated with the same brightness when the distance between the lamp body 4 and the operation site is changed.

Additionally, in some embodiments, the surgical lamp 1 optionally includes an actuator and means for transmitting the actuation information to the control device 7. The permanent adjustment of the distance of the point having the maximum resulting brightness can be disruptive to the surgeon because when an obstacle, such as an instrument, hands, or the head of the surgeon, is brought into the path of the light beam I, I', II, III, the distance of the point is adjusted due to the perceived change in distance of the operation site. The actuator allows the adjustment of the point having the maximum resulting brightness at moments which are desired by the surgeon.

FIG. 3 is a sectional view of the lamp body 4 with its illuminants 9. The lamp body 4 includes a housing 14 made of aluminum or a suitable resin material. A fixing face 15 for each illuminant 9 is provided in the housing 14.

The fixing faces 15 are provided in such a way that the illuminants are arranged in a plane that is perpendicular to the central axis 12 of the lamp body 4. As a result, a flat design is achieved. Due to the flatness of the lamp body 4, the lamp body 4 rarely influences the laminar airflow of a low-turbulence displacement air flow.

The fixing faces 15 are inclined compared to the central axis 12 so that axes that are perpendicular to the fixing faces 15 are parallel to the respective axis a, a', b, c and intersect the central axis 12 at the intersection points 13, 13' and 13". Thus, the identical illuminants 9 with refractors 10 can be used at all fixing faces 15 and only small diameter differences occur when the distances are different.

Other embodiments are within the scope of the following claims.

What is claimed is:

1. A surgical lamp, comprising
 a lamp body having a central axis, the lamp body comprising a group of first illuminants and a group of second illuminants, each of the first and second illuminants being configured to emit a bundle of light beams, the group of first illuminants being configured such that the bundles of light beams emitted by the first illuminants overlap to produce a first light field and the group of second illuminants being configured such that the bundles of light beams emitted by the second illuminants overlap to produce a second light field,
 wherein an axis of the bundle of light beams emitted by each of the first illuminants is directed to a first point on the central axis, an axis of the bundle of light beams emitted by each of the second illuminants is directed to a second point on the central axis, and the first and second points are spaced apart from one another along the central axis such that the first and second points are positioned at different distances from the lamp body along the central axis and the first and second light fields are positioned at different distances from the lamp body along the central axis, and wherein the axis of each bundle of light beams extends along a center line of its respective bundle of light beams.

2. The surgical lamp of claim 1, further comprising a device adapted to dim the illuminants and to turn the illuminants on and off.

3. The surgical lamp of claim 2, wherein the device is a current regulator.

4. The surgical lamp of claim 1, wherein the illuminants are arranged in a plane that is perpendicular to the central axis.

5. The surgical lamp of claim 1, wherein the illuminants of at least one of the groups are evenly distributed across the lamp body.

6. The surgical lamp of claim 1, wherein the illuminants of at least one of the groups are arranged in an annular pattern about the central axis of the lamp body.

7. The surgical lamp of claim 1, wherein each of the illuminants is attached to an inclined fixing face of a housing of the lamp body.

8. The surgical lamp of claim 7, wherein each of the inclined faces has an axis that extends perpendicularly relative to the inclined face, and the axes of the inclined faces to which the illuminants of one of the groups are attached intersect the central axis at a common location along the central axis.

9. The surgical lamp of claim 1, further comprising a control device adapted to operate the groups of illuminants in a manner so that the illuminants that emit the bundles of light beams whose axes are directed nearest a desired operation site have the greatest brightness.

10. The surgical lamp of claim 1, wherein the illuminants are attached to inclined fixing faces of a housing of the lamp body.

11. The surgical lamp of claim 1, wherein the illuminants comprise light emitting diodes.

12. The surgical lamp of claim 1, wherein the illuminants comprise light emitting diodes and refractors.

13. The surgical lamp of claim 1, wherein the illuminants comprise light emitting diodes and reflectors.

14. The surgical lamp of claim 1, further comprising a control device adapted to operate the illuminants in a manner so that the illuminants that emits the bundles of light beams whose axis intersects the central axis of the lamp body nearest an operation site has the greatest brightness.

15. The surgical lamp of claim 14, wherein the surgical lamp comprises a distance sensor configured to measure a distance between the lamp body and the operation site.

16. The surgical lamp of claim 14, wherein the surgical lamp comprises a brightness sensor configured to measure brightness at the operation site.

17. The surgical lamp of claim 14, wherein the surgical lamp comprises an actuator that is adapted to transmit actuation information to the control device.

18. The surgical lamp of claim 15, wherein the distance sensor is adapted to transmit distance information to the control device, and the control device is adapted to operate the illuminants based on the distance information received from the distance sensor.

19. The surgical lamp of claim 18, wherein the control device is adapted to operate the group of illuminants configured to emit bundles of light beams whose axis are nearest the operation site at a greater brightness than the other group of illuminants.

20. The surgical lamp of claim 16, wherein the brightness sensor is adapted to transmit brightness information to the control device.

* * * * *

UNITED STATES PATENT AND TRADEMARK OFFICE
CERTIFICATE OF CORRECTION

PATENT NO. : 8,292,804 B2  
APPLICATION NO. : 12/487239  
DATED : October 23, 2012  
INVENTOR(S) : Rudolf Marka, Rouven Rosenheimer and Dirk Fritze Page 1 of 1

It is certified that error appears in the above-identified patent and that said Letters Patent is hereby corrected as shown below:

Column 8, line 36 (Claim 14, line 36), delete "operate the" and insert --operate the groups of--.

Column 8, line 37 (Claim 14, line 37), delete "emits" and insert --emit--.

Column 8, line 38 (Claim 14, line 38), delete "axis intersects" and insert --axes intersect--.

Column 8, line 56 (Claim 19, line 56), delete "axis" and insert --axes--.

Signed and Sealed this  
Twenty-second Day of January, 2013

David J. Kappos  
*Director of the United States Patent and Trademark Office*